United States Patent [19]

Ohtomo et al.

[11] Patent Number: 5,348,009
[45] Date of Patent: Sep. 20, 1994

[54] BONE ASSESSMENT APPARATUS

[75] Inventors: Naoki Ohtomo; Shigeo Kimura, both of Tokyo, Japan

[73] Assignee: Aloka Co., Ltd., Tokyo, Japan

[21] Appl. No.: 63,779

[22] Filed: May 20, 1993

[30] Foreign Application Priority Data

May 20, 1992 [JP] Japan .................. 4-127551
Feb. 22, 1993 [JP] Japan .................. 5-031672

[51] Int. Cl.$^5$ .................. A61B 5/00; A61B 6/00; A61B 8/00
[52] U.S. Cl. .................. 128/653.1; 128/660.01; 128/661.03; 73/597; 378/89; 378/54
[58] Field of Search .......... 128/653.1, 660.01, 660.06, 128/661.02, 661.03; 378/87, 88, 89, 54; 73/597, 598, 599, 602

[56] References Cited

U.S. PATENT DOCUMENTS

| | | | |
|---|---|---|---|
| 4,721,112 | 1/1988 | Hirano et al. ............ | 128/653.1 |
| 4,829,549 | 5/1989 | Vogel et al. ............ | 128/653.1 |
| 4,913,157 | 4/1990 | Pratt, Jr. et al. ......... | 128/661.03 |
| 4,976,267 | 12/1990 | Jeffcott et al. .......... | 128/660.01 |
| 5,134,999 | 8/1992 | Osipov .................. | 128/661.03 |
| 5,197,475 | 3/1993 | Antich et al. ........... | 128/660.01 |
| 5,218,963 | 6/1993 | Mazess .................. | 128/661.03 |
| 5,247,560 | 9/1993 | Hosokawa et al. ......... | 378/89 |
| 5,259,384 | 11/1993 | Kaufman et al. .......... | 128/661.03 |

FOREIGN PATENT DOCUMENTS 0480554  4/1992  European Pat. Off. .

OTHER PUBLICATIONS

European Search Report dated Sep. 27, 1993.
Andre, Michael P. et al., "Measurement of the velocity of ultrasound in the human femur in vivo," Medical Physics, vol. 7 (1980) Jul./Aug., pp. 324–330.

*Primary Examiner*—K. M. Pfaffle
*Attorney, Agent, or Firm*—Fish & Richardson

[57] ABSTRACT

An apparatus for providing assessment indices related to bone strength which are useful in predicting the risk of bone fracture. The apparatus measures the mineral density of bone (BMD) by means of X-rays, while the propagation speed of sound V in the bone and bone thickness d are measured by means of ultrasonic waves. The bone mineral content per unit volume, i.e. the bone volume density $\rho$, is computed from the bone mineral density (BMD) and the thickness of the bone. An assessment value E is then computed based on V and $\rho$.

15 Claims, 12 Drawing Sheets

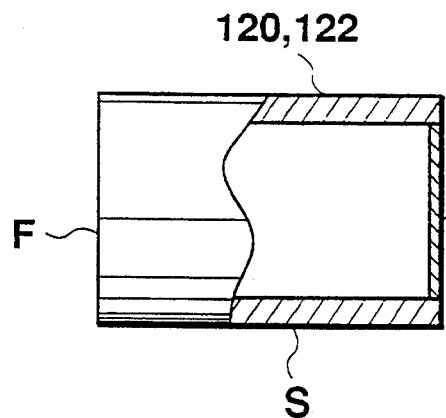
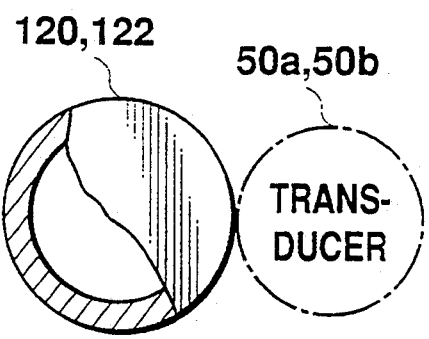
Fig. 17    Fig. 18
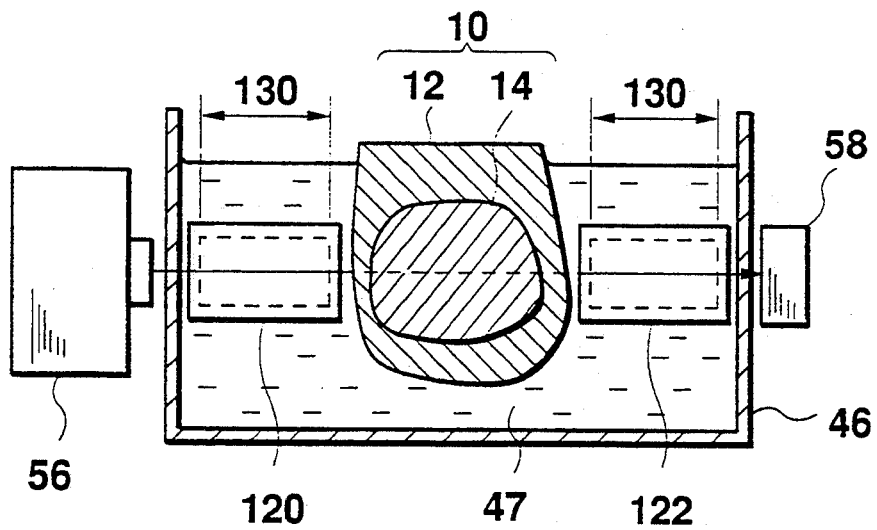
Fig. 19

BONE ASSESSMENT APPARATUS

BACKGROUND OF THE INVENTION

Field of the Invention

This invention relates to a bone assessment apparatus, and more particularly to an apparatus which provides new information about bone quality useful in diagnosing bone disorders.

Description of the Related Art

Due to the rapid increase in the number of elderly people in the population, bone disorders such as osteoporosis and osteomalacia are becoming more common, and a great need has emerged for better diagnosis and prophylaxis.

Bones are composed of minerals such as calcium, and a bone matrix.

Osteoporosis generally refers to a disorder wherein the proportion of bone matrix to minerals is normal, but the amount of bone decreases. Osteomalacia generally refers to a disorder wherein only the mineral content decreases due to osteopetrosis. The bone composition therefore varies depending on the type of disorder.

In any case, the bone tends to fracture when it becomes weaker, and this tendency is particularly evident in elderly people.

Conventionally, an apparatus for diagnosing bone mineral content has been used to diagnose bone disorders. This apparatus irradiates a subject with X-rays from the outside of the body, and analyzes the bone mineral content (of minerals such as calcium) from the X-ray attenuation factor. Osteoporosis is then diagnosed from the magnitude of the mineral content thereby determined. In a conventional appratus, the bone mineral content is computed per unit area ($g/cm^2$).

Bone strength, however, does not depend only on bone mineral content. Bone mineral content is certainly the major factor which determines bone strength, but this strength is also influenced by other factors such as bone rigidity, elasticity and structure.

In other words, the bone strength may be low even if the bone mineral content is high so that fractures can easily occur. Conversely, the bone strength may be high even if the bone mineral content is low so that fractures do not occur easily.

Therefore, in order to assess the risk of a fracture, it is often insufficient to make the assessment solely on the basis of the bone mineral content, and it is then necessary to know something about "bone strength".

SUMMARY OF THE INVENTION

This invention, which was conceived to overcome the aforesaid problems in the conventional technology, aims to provide a bone assessment apparatus which analyzes new criteria related to bone indicative of bone strength.

This invention also aims to perform "a bone assessment" based on ultrasonic wave measurements and X-ray measurements.

In order to achieve the aforesaid objectives, this invention provides a means for measuring the propagation speed of sound in bone by passing ultrasonic waves through a test part of a bone, a means for measuring the mineral content per unit volume (bone volume density) by passing X-rays through the aforesaid test part of bone, and a means for computing "a bone assessment" index defined from the aforesaid propagation speed of sound in bone and bone volume density.

According to this construction, the propagation speed of ultrasonic waves in the bone is measured by transmitted and received signals, and the bone volume density is measured by X-ray irradiation. The bone assessment index is then computed from these two measured values.

This bone assessment index is defined as the result of multiplying the aforesaid square of the propagation speed of sound in bone by the bone volume density. The index also corresponds to a bone elasticity coefficient.

The means of measuring the propagation speed of sound in bone comprises a pair of ultrasonic transducers for transmitting and receiving ultrasonic waves through the test part of the bone, a thickness computer for computing the thickness of bone in the direction of the X-ray beam based on the signal received from the aforesaid ultrasonic transducer, and a propagation speed computer for computing the propagation speed of sound in the bone by dividing the ultrasonic signal propagation time in the bone by the thickness.

The means for measuring the bone volume density comprises an X-ray generator for irradiating the test part of the bone with X-rays, an X-ray detector for detecting X-rays which have passed through the aforesaid test part, and a density computer for computing the bone volume density based on the X-ray detection signal from the X-ray detector and the bone volume thickness value from the thickness computer.

According to this invention, a water tank containing a matching material is used in order to improve the propagation of the ultrasonic signals.

An immersible body is filled with a material having a lower X-ray attenuation coefficient than water, or contains a vacuum, and is disposed in the path of the X-rays. By using this immersible body, the attenuation of X-rays is reduced.

The cylindrical side wall enclosing the immersible body is constructed of a shielding material having a high X-ray attenuation coefficient. The immersible body therefore has a collimating effect. Further, as the immersible body sinks in water, the amount of water used can be accordingly reduced.

BRIEF DESCRIPTION OF THE DRAWINGS

FIG. 17 is a drawing of the hollow bodies 120, 122 as seen from the side.

FIG. 18 is a drawing of the hollow bodies 120, 122 as seen from the front.

FIG. 19 is a drawing showing the path traversed by the X-rays.

DESCRIPTION OF THE PREFERRED EMBODIMENTS

The preferred embodiments of the invention will now be described with reference to the drawings.

(A) Explanation of Principle

The propagation speed V of ultrasonic waves in an anisotropic medium such as bone may be expressed by a function of the bone volume density $\rho$ and the elasticity E. This can be represented in the form of a general equation:

$$V = k \cdot (E/\rho)^{\frac{1}{2}} \quad (1)$$

where k is a constant. The bone volume density $\rho$ (g/cm$^3$) corresponds to the bone mineral density BMD (g/cm$^2$) as measured by X-rays using a conventional bone mineral content assessment apparatus divided by the bone thickness d (cm). The propagation speed V of ultrasonic waves is measured from the transmitted and received signals:

The modulus of elasticity (Young's Modulus) E is given by the following relation:

$$E = k' \cdot V^2 \cdot \rho \quad (2)$$

where $\rho = BMD/d$, $k' = k^{-2}$

In the case of bone, the modulus of elasticity E may be considered to represent the strength of the bone such as tensile strength and rigidity, etc. In other words, the value of E may be considered as a physical property expressing the risk of bone fracture.

According to this invention, this value E is defined as an "assessment index" of the bone.

Various formulae for calculating the modulus of elasticity of bone are known. Other definitions may be used as indicators of bone strength, but as far as concerns this invention, assessment indices will be defined on the basis of the modulus of elasticity.

(B) Basic Structure of Bone Assessment Apparatus

Figure 1:
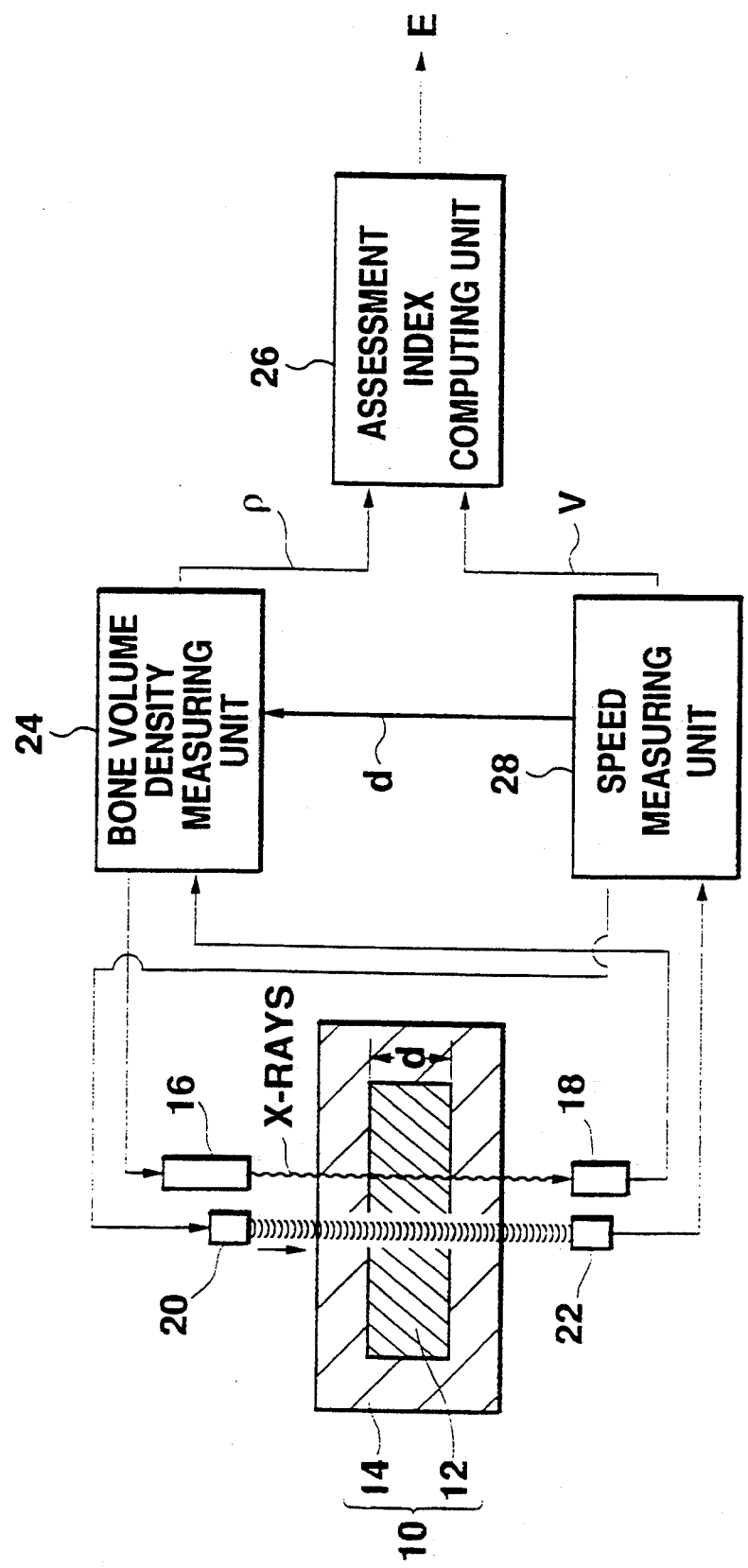
FIG. 1 is a block diagram showing the measuring principle of this invention.

In FIG. 1, a (living) subject 10 generally consists of bone 12 and soft tissue 14. An X-ray generator 16 for generating X-rays, and an X-ray detector 18 for detecting X-rays which have passed through the subject 10, are disposed in the vicinity of the subject 10.

Transmitter transducer 20 and receiver transducer 22 are disposed near the X-ray generator 16 and X-ray detector 18 in the vicinity of the subject 10. When measuring the bone thickness d, the transducers 20 and 22 are used for both transmitting and receiving.

The bone volume density measuring unit 24 supplies a driving signal to the X-ray generator 16 and receives a detection signal from the X-ray detector 18 in order to measure the bone volume density $\rho$ of the bone 12. This bone volume density $\rho$ is sent to a computing unit 26 for computing the bone assessment index E.

A propagation speed measuring unit 28 supplies an exciting signal to the transducer 20 and receives a signal from the transducer 22 in order to compute the propagation speed V of ultrasonic waves in the bone 12. This propagation speed V is sent to the bone assessment index computing unit 26.

The bone assessment index computing unit 26 executes the above Equation 2, and computes the assessment index E based on the bone volume density $\rho$ and propagation speed V. This E is then output, and for example displayed on a display or the like. The risk of fracture of the bone can then be assessed based on the magnitude of this assessment index E, or a diagnosis of osteoporosis or another disorder can be made.

The structure of bone however broadly comprises cancellous bone and cortical bone. It is said that the metabolic rate of cancellous bone is about 8 times higher than that of cortical bone. For this reason, osteopenia or decrease of bone strength is likely to occur first in cancellous bone.

Tests are therefore usually performed on cancellous bone. For example, the calcaneus or the lumbar spine can be measured, and the accuracy of diagnosis is thereby improved.

In the bone assessment apparatus of this embodiment described hereinafter, the calcaneus is used for measurements.

(C) Detailed Structure of Bone Assessment Apparatus

Figure 2:
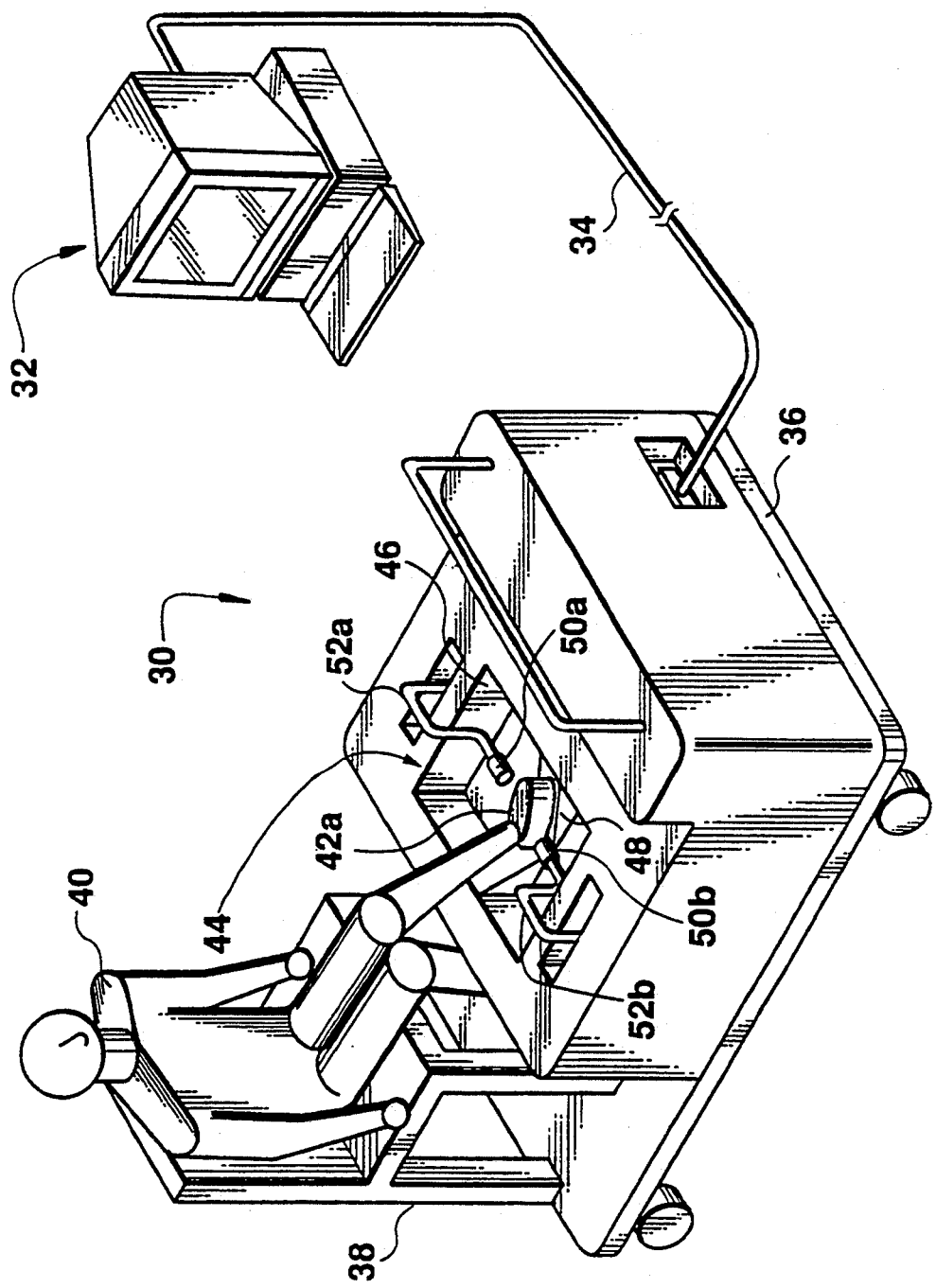
FIG. 2 is a perspective view showing the external appearance of the bone assessment apparatus according to this invention.

The external appearance of a bone assessment apparatus according to this embodiment is shown in FIG. 2. This bone assessment apparatus comprises a scanner unit 30, and a control unit 32.

As shown in the figure, the control unit 32 consists of a computer or the like, and is connected to the scanner unit 30 by means of a cable 34.

In the scanner unit 30, a plurality of casters are provided on the underside of a trolley 36, a chair 38 and a measuring unit 44 being mounted on the trolley 36. This measuring unit 44 comprises a water tank 46, and a foot rest 48 is provided in the tank 46.

To perform a measurement, a subject 40 sits in the chair 38 and places one of his feet 42a on the foot rest 48 in the tank 46. X-ray measurements and ultrasonic measurements can then be made.

The outer wall of the tank 46 consists of a material which has a low X-ray attenuation, for example acrylic sheet.

The reason why the foot 42a is placed in the water tank 46 is because water has the same X-ray attenuation and acoustic propagation speed as the soft tissue of a living body. If this construction is adopted, therefore, bone can be measured irrespective of the shape of the soft tissue.

As shown in the drawing, in the measuring unit 44, two ultrasonic transducers 50a, 50b supported by arms 52a, 52b are disposed on either side of the foot 42a. In FIG. 2, the X-ray generator and X-ray detector are not shown.

(D) Construction of Measuring Unit

Figure 3:
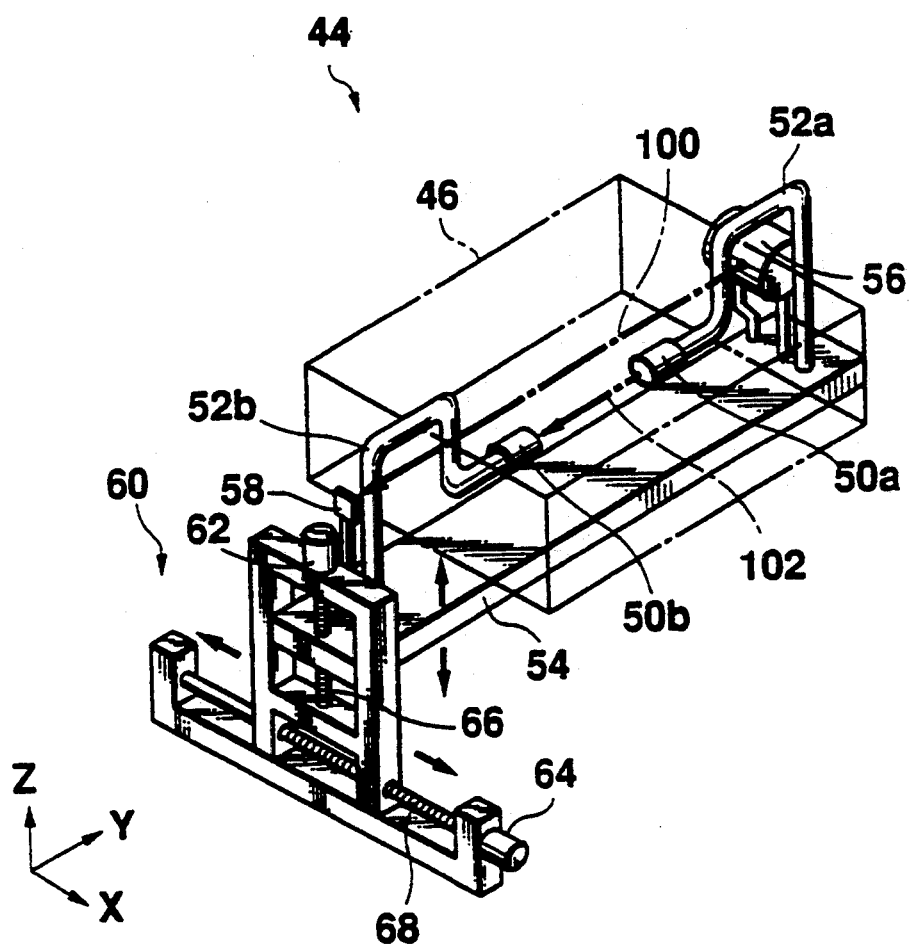
FIG. 3 is a perspective view of a measuring unit 44.

FIG. 3 is a perspective view showing the main parts of the measuring unit 44. In the figure, the water tank 46 is shown by a dashed line.

The arm 52a and an X-ray generator 56 are installed at one end of a platform 54. A collimator or filter, neither of which are shown, are disposed at the radiation aperture of the X-ray generator 56.

The arm 52b and an X-ray detector 58 consisting of a semiconductor detector or the like, are disposed at the other end of the platform 54. X-rays are generated from outside the tank 46, and after passing through the foot inside the tank, are measured outside the tank.

The platform 54 is supported by a displacing mechanism 60. This displacing mechanism 60 comprises a Z direction lifting unit for raising and lowering the platform 54 in the Z direction, and an X direction displacement unit for moving the platform 54 in the X direction. These units comprise motors 62, 64 and feed screws 66, 68. The platform 54 can be freely moved in the X and Z directions by rotating the screws 66, 68 by means of the motors 62, 64.

As shown in FIG. 3, X-rays 100 are collimated to a narrow beam which are allowed to irradiate the subject, and ultrasonic waves 102 are transmitted and received on a line connecting the ultrasonic transducers 50a, 50b. The X-ray beam and ultrasonic beam are adjacent to one another.

(E) Structure of Scanner Unit

Figure 4:
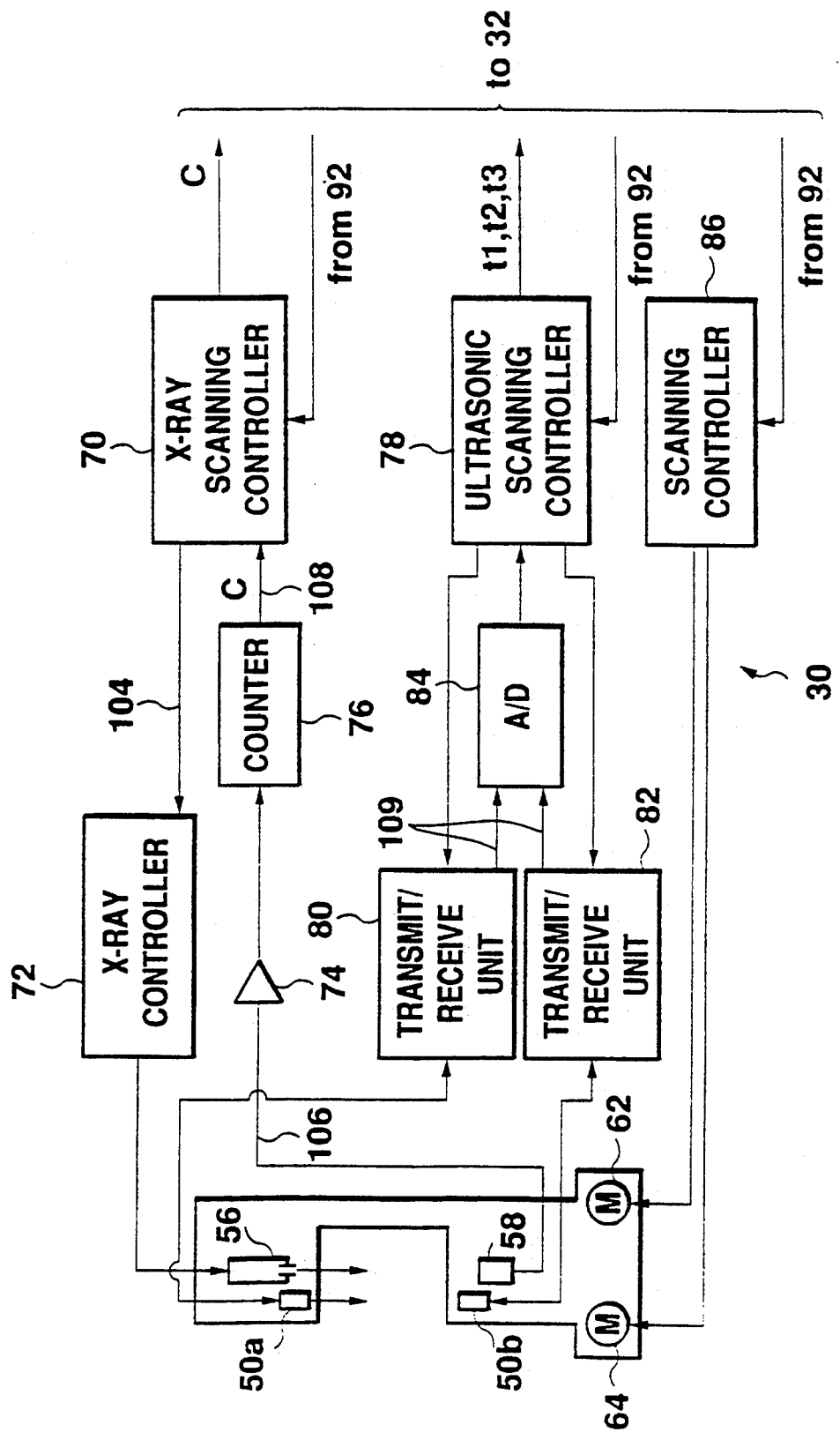
FIG. 4 is a block diagram showing the construction of a scanner unit 30.

FIG. 4 shows a block diagram of the structure of the scanner unit 30 shown in FIG. 2.

An X-ray scanning controller 70 controls the generation and detection of X-rays. A driving signal 104 output by the X-ray scanning controller 70 is sent to the X-ray generator 56 via an X-ray controller 72. The X-ray controller 72 determines a driving voltage of the X-ray generator 56.

An X-ray detection signal 106, output by the X-ray detector 58 which detects X-rays, is amplified by an amplifier 74, and input to a counter 76. This counter 76 computes the intensity of the X-rays by counting pulses, and a signal 108 showing a count rate C is sent from the counter 76 to the X-ray scanning controller 70. The signal 108 indicating this count rate C is also sent to the control unit 32.

An ultrasonic scanning controller 78 controls transmitted and received ultrasonic signals. It controls a first transmit/receive unit 80 and a second transmit/receive unit 82, these transmit/receive units 80, 82 each comprising a transmitter and a receiver. The first transmit/receive unit 80 transmits an exciting signal to the ultrasonic transducer 50a, and receives a signal from the ultrasonic transducer 50a. The second transmit/receive unit 82, similarly to the first transmit/receive unit 80, supplies an exciting signal to and receives a signal from the ultrasonic transducer 50b.

Received signals 109 output from the transmit/receive units 80, 82 are converted to digital values by an A/D converter 84, and are sent to the ultrasonic scanning controller 78.

Times t1, t2, t3 described hereinafter are then measured by this ultrasonic scanning controller 78, and these time data are output to the control unit 32.

A scanning controller 86, which controls the up/down and forward/backward motion of the platform 54, outputs driving signals to the motors 62 and 64.

These scanning controllers 70, 78, 86 are all controlled by the control unit 32.

(F) Structure of Control Unit

Figure 5:
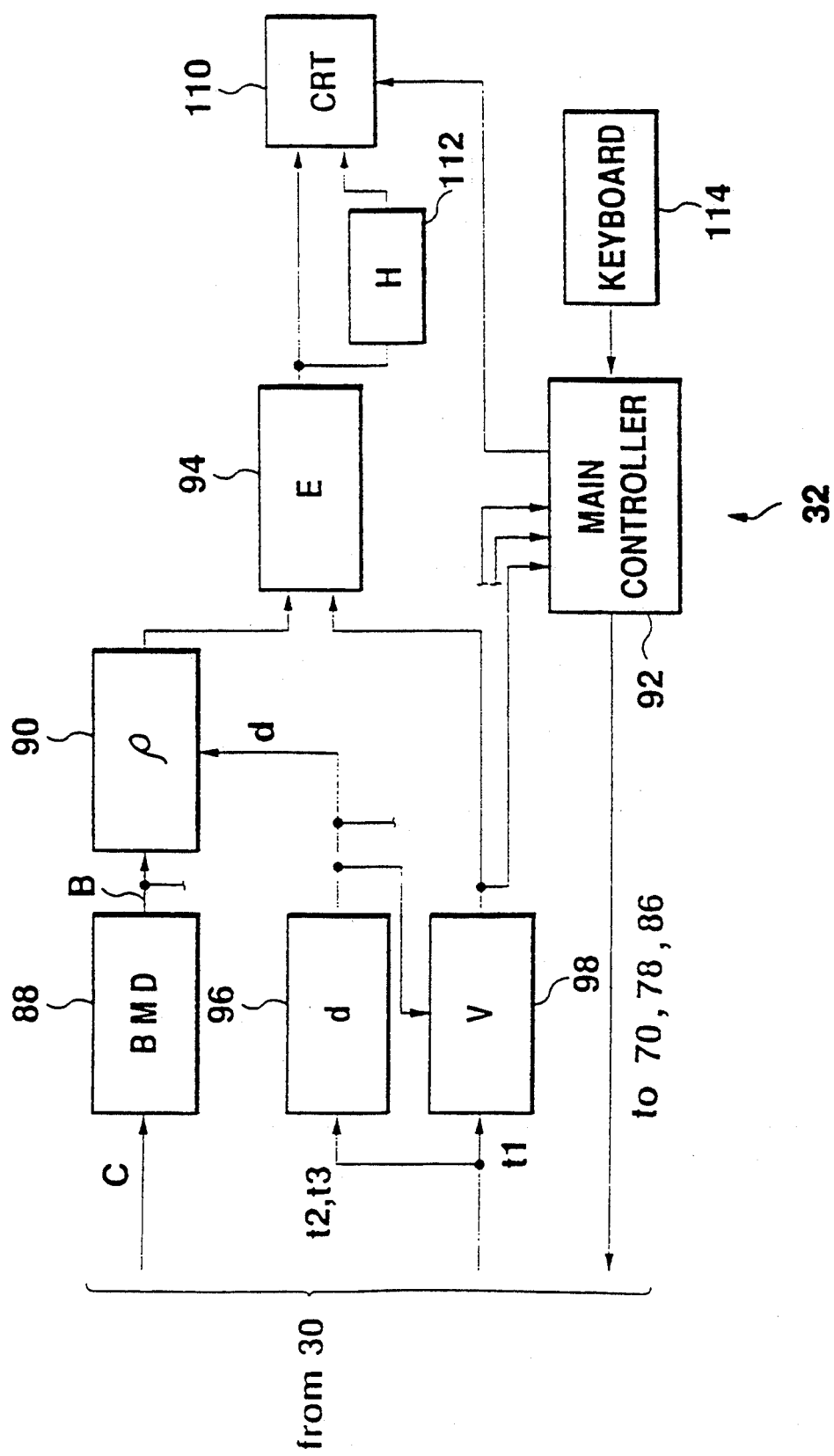
FIG. 5 is a block diagram showing the construction of a control unit 32.

In FIG. 5, the detailed structure of the control unit 32 illustrated in FIG. 2 is shown by a block diagram. The count rate C indicating the intensity of the X-rays is input to a BMD computer 88 for computing bone mineral density (g/cm$^2$). The result B of this computation is sent to a bone volume density computer 90 and a main controller 92. The bone volume density computer 90 computes a mineral content per unit volume (g/cm$^3$) by dividing the bone mineral content B by the bone thickness d, and the result $\rho$ of this computation is output to an assessment index computer 94.

A thickness computer 96 computes a bone thickness d based on t1, t2, t3 as described hereinafter. The result d of this computation is output respectively to the aforesaid bone volume density computer 90, an acoustic speed computer 98, and the main controller 92.

The acoustic speed computer 98 computes the propagation speed V of ultrasonic waves in bone based on t1 and d. The result V of this computation is output to the assessment index computer 94 and the main controller 92.

The assessment index computer 94 performs the computation of Equation 2 described hereinabove based on the aforesaid bone volume density $\rho$ and acoustic speed V, and calculates an assessment index E. This assessment index E is output to a CRT 110.

According to this embodiment, a health index computer 112 is provided which computes a bone health index H based on the assessment index E which is output to the CRT 110.

The main controller 92 controls the whole assessment apparatus, and also controls the X-ray scanning controller 70, ultrasonic scanning controller 78 and scanning controller 86. A keyboard 114 is connected to the main controller 92.

(G) Operation of Bone Assessment Apparatus

As shown in FIG. 2, when performing a bone assessment, the subject 40 is made to sit in the chair 38, and one of his feet 42a is placed in the water tank 46. The operator then commands a measurement to be performed from the keyboard 114 shown in FIG. 5. When this occurs, the main controller 92 of FIG. 5 commands the scanning controller 86 shown in FIG. 4 to set the assessment apparatus to an initial position. The scanning controller 86 controls the motors 62, 64 so as to move the irradiating positions of the X-rays and ultrasonic waves to this initial position. After this position has been set, the main controller 92 shown in FIG. 5 commands the X-ray scanning controller 70 shown in FIG. 4 to perform an X-ray measurement.

The driving signal 104 is sent from the X-ray scanning controller 70 via the X-ray controller 72 to the X-ray generator 56 and the subject's foot is irradiated by X-rays.

X-rays which have passed through the subject's foot 42a are detected by the X-ray detector 58, the detection signal 106 is input to the counter 76 via the amplifier 74, and counting is performed. A signal C 108 which indicates a count value is then sent to the BMD computer 88 shown in FIG. 5 via the X-ray scanning controller 70, the bone mineral density B is computed (g/cm$^2$), and this bone mineral density B is sent to the bone volume density computer 90.

After this X-ray measurement has been performed, an ultrasonic wave measurement is carried out.

Figure 6:
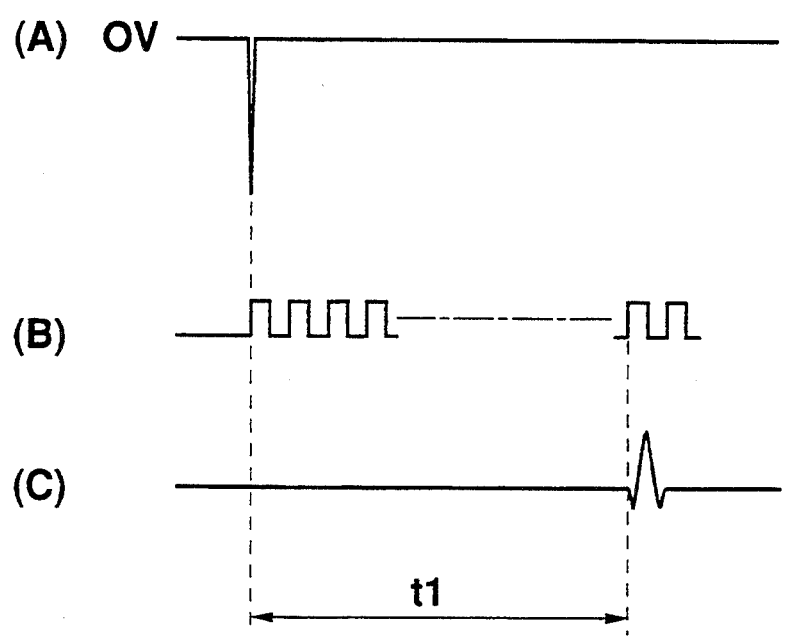
FIG. 6 is a waveform diagram showing the signals involved in ultrasonic wave measurement.

A command is first given by the main controller 92 to the ultrasonic scanning controller 78 of FIG. 4, and the ultrasonic scanning controller 78 outputs a pulse indicating a transmit command to the first transmit/receive unit 80 (FIG. 6(A)). At the same time, the ultrasonic scanning controller 78 starts an internal counter (FIG. 6(B)). An exciting signal is then sent from the first transmit/receive unit 80 to the ultrasonic transducer 50a so as to transmit ultrasonic waves to the foot 42a, and the ultrasonic waves which have passed through the foot are received by the ultrasonic transducer 50b. The received signal obtained, which is shown in FIG. 6(C), is then sent to the ultrasonic scanning controller 78 via the second transmit/receive unit 82 and the A/D converter 84.

The ultrasonic scanning controller 78 reads the count value until the received pulse shown in FIG. 6(C) is obtained, and the time t1 represented by this count value is output to the control unit 32.

Next, a thickness measurement is performed on the bone (calcaneus).

Before describing how the assessment apparatus measures thickness, the principle of measuring bone thickness will first be described.

Figure 7:
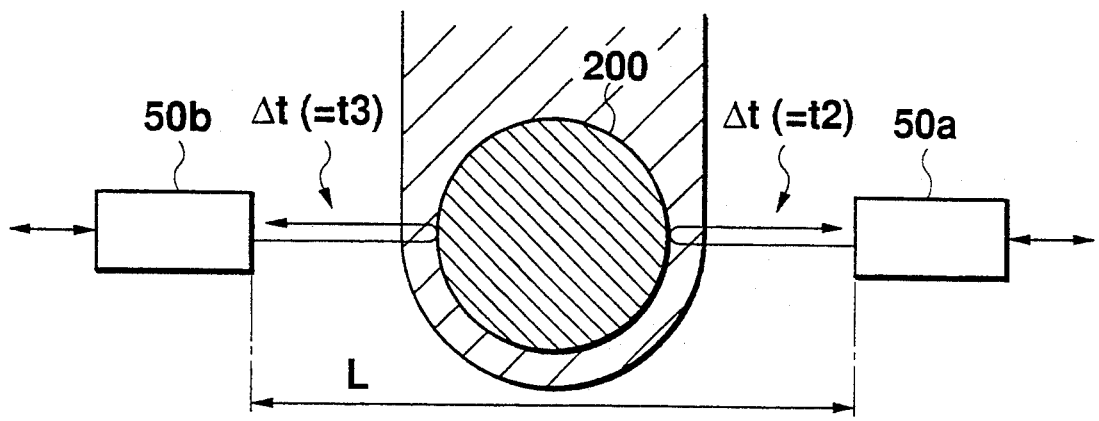
FIG. 7 is a diagram showing the method used for measuring bone thickness.

According to this embodiment, as shown in FIG. 7, ultrasonic waves are transmitted from one side of the calcaneus 200 by the ultrasonic transducer 50a, and ultrasonic waves reflected by the surface of the calcaneus are measured by this ultrasonic transducer 50a. Ultrasonic waves are also transmitted and received by the ultrasonic transducer 50b on the other side of the calcaneus 200.

As water has practically the same acoustic propagation characteristics as soft tissue, the thickness d of the calcaneus 200 is easily computed from the transmit/receive time $\Delta t$ on one side of the calcaneus and the transmit/receive time $\Delta t$ on the other side of the calcaneus. The propagation speed $V_w$ of sound in water is known, so the thickness d can be computed from the following Equation 3:

$$d = L - (t2 + t3) \cdot (V_w/2) \quad (3)$$

where L = inter-transducer distance.

Figure 8:
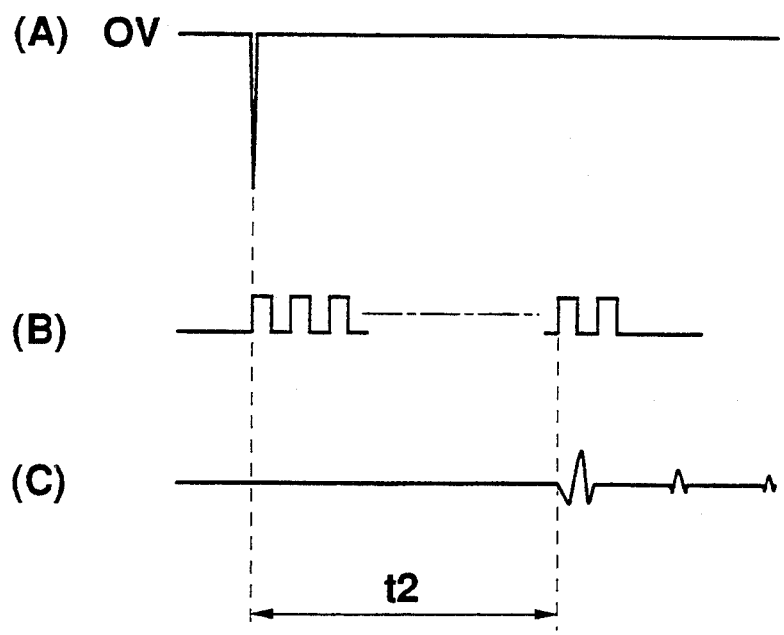
FIG. 8 is a waveform diagram showing the signals involved in ultrasonic wave measurement.

In order to implement the above principle, the main controller 92 issues a command to measure the thickness. The ultrasonic scanner unit 78 first outputs a pulse to the first transmit/receive unit 80, as shown in FIG. 8(A), and this starts an internal counter as shown in FIG. 8(B). An exciting signal is then output by the first transmit/receive unit 80 to the ultrasonic transducer 50a, and after transmitting this ultrasonic signal, the reflected acoustic signal is received by the transducer 50a. The received acoustic signal shown in FIG. 8(C) is sent to the ultrasonic scanner unit 78 via the A/D converter 84. The scanner unit 78 detects the pulse in the received acoustic signal, and a transmit/receive time t2 is found from the pulse count starting from the time when counting is begun to when the pulse is received. This time t2 is sent to the control unit 32.

The measurement of t3 is the same as described hereinbefore, i.e. the second transmit/receive unit 82 is activated, a measurement is taken, and t3 is sent to the control unit 32.

Times t2, t3 which are obtained as described hereinbefore are sent to the thickness computer 96 of FIG. 5, Equation 3 is executed, the bone thickness d is found, and this thickness d is sent to the bone volume density computer 90 and the acoustic speed computer 98. The bone volume density computer 90 then executes the following Equation 4:

$$\rho = B/d \ (g/cm^3) \quad (4)$$

The acoustic speed computer 98 to which t1 is input computes the acoustic speed V according to the following Equation (5):

$$V = d/\{t1 - (t2 + t3)/2\} \quad (5)$$

Based on $\rho$ and V obtained as described hereinabove, the assessment value computer 94 executes Equation 2, i.e. $E = k \cdot V^2 \cdot \rho$ in order to find the assessment index E.

After the aforesaid process has been performed for a given measurement site, the measurement point is shifted by the scanner unit 86 and the process is repeated.

Figure 9:
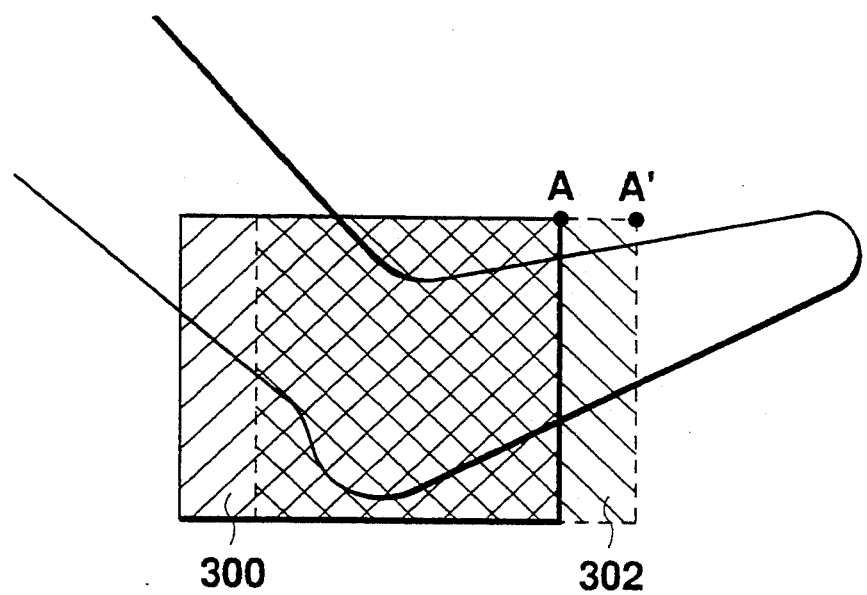
FIG. 9 is a drawing showing an area irradiated by X-rays and ultrasonic waves.

FIG. 9 shows areas irradiated by X-rays and ultrasonic waves. In the figure, 300 is an area irradiated by X-rays, and 302 is an area in which ultrasonic waves are transmitted and received. Both areas are of sufficient size to cover the calcaneus.

In the case described herein the ultrasonic transducer and X-ray generator are installed a short distance away from each other, so the areas 300 and 302 are also slightly displaced with respect to one another.

A and A' in FIG. 9 are the aforementioned initial positions. A is the initial X-ray position, and A' is the initial ultrasonic wave position. As described hereinbefore, after the subject has been irradiated in the initial position, the irradiation position is shifted a little to the left or downwards in the figure, then the irradiation and scanning are repeated. The entire process is repeated several times so that finally, data is obtained for the whole area shown in FIG. 9. After irradiating with X-rays, the ultrasonic transmit/receive point can be shifted to the point that was irradiated by X-rays so that the two areas 300 and 302 shown in FIG. 9 coincide.

Figure 10:
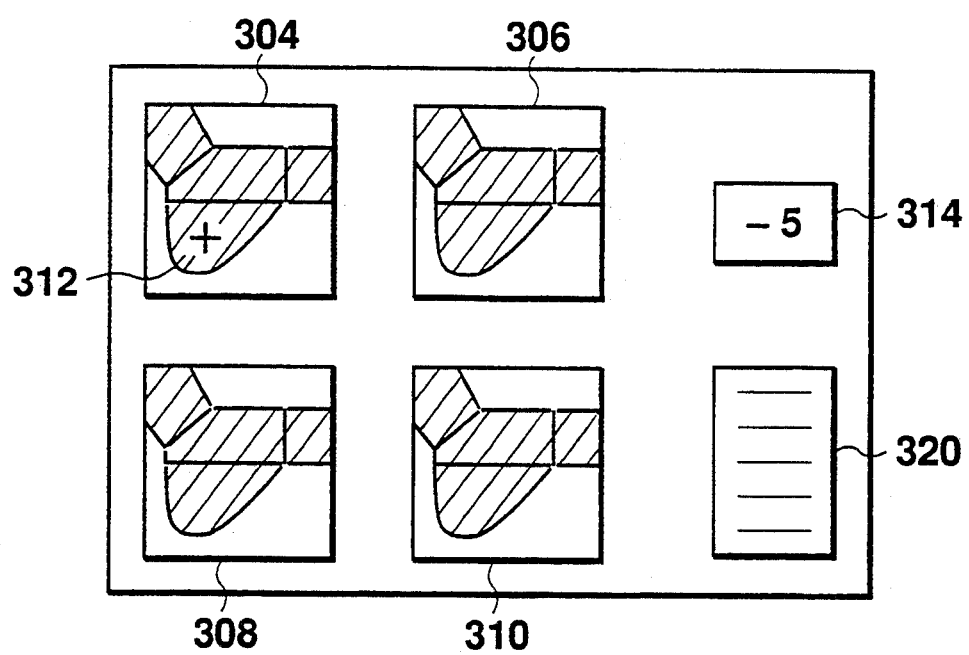
FIG. 10 is a drawing showing a typical bone assessment index display.

FIG. 10 shows an example of the display on the CRT 110. In the figure, 304 is a bone mineral density map showing the distribution of bone mineral density B, 306 is a thickness map showing the thickness d of the bone (calcaneus), 308 is an ultrasonic wave map showing the propagation speed of ultrasonic waves in the bone, and 310 is an assessment index map showing assessment indices E calculated by the aforesaid computation. In the figure, 312 represents a cursor.

314 is an index indicating the health of the bone at the position specified by the cursor 312, and is calculated based on E as follows.

Figure 11:
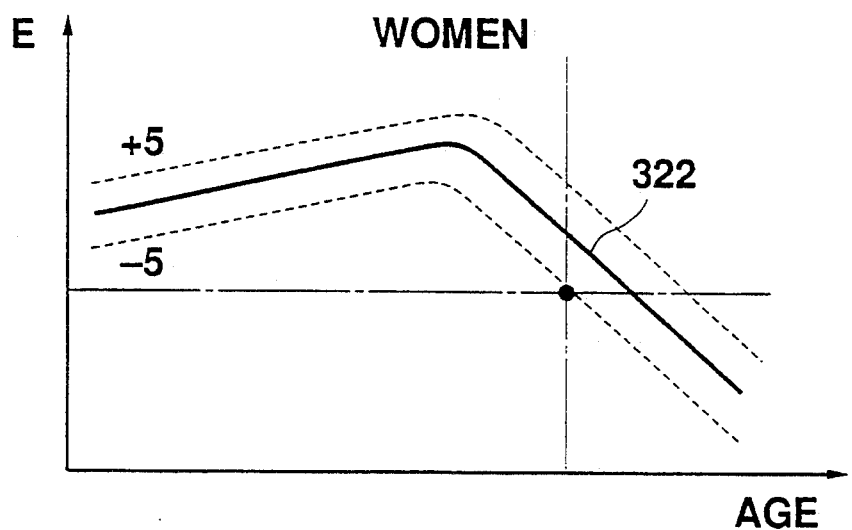
FIG. 11 is a drawing showing a graph representing the relationship between age and a bone assessment index E.

FIG. 11 is a normal reference curve 322 showing reference values of E at various ages. The health index 314 which is displayed shows how far a point specified by the subject's age and the actual measured assessment index E, is from the reference curve 322.

More specifically, the actual measured assessment index is subtracted from the standard value for the age in question, and the difference is expressed as the health index 314.

The data display 320 in FIG. 10 displays the bone mineral density, thickness, sound propagation speed and assessment index in numeric form for the measured part of the bone specified by the cursor 312.

By displaying this information on the CRT 110, various useful data concerning the bone can be shown alongside when diagnosing bone disorders such as bone osteoporosis.

Figure 12:
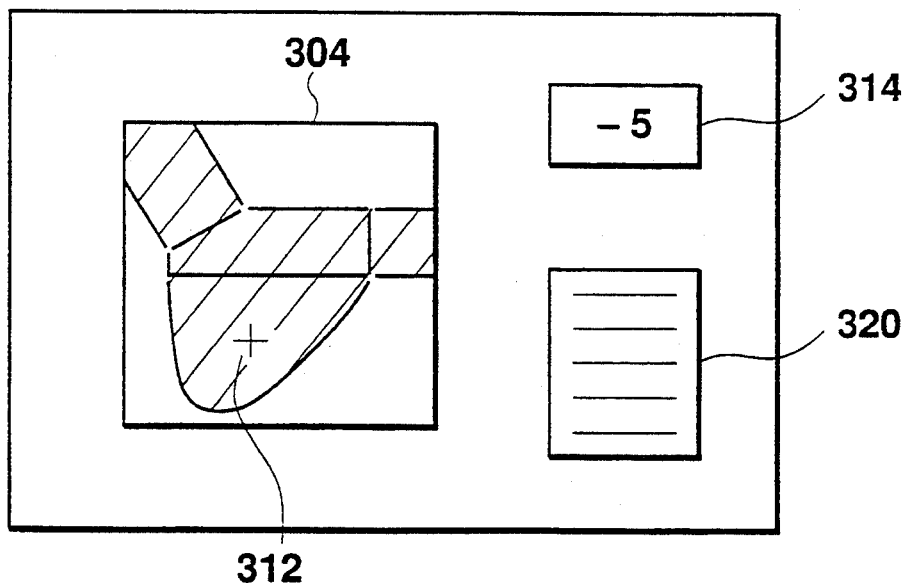
FIG. 12 is a drawing showing another typical display of the bone assessment index E.

In the aforesaid embodiment, the whole of the calcaneus was irradiated by X-rays and ultrasonic waves, but the following modification is also possible. As shown by the display in FIG. 12, X-ray irradiation is first performed so as to display only the bone mineral content map 304. The operator then moves the cursor 312 to specify an area where it is desired to calculate the assessment index E. This area alone is subjected to ultrasonic wave irradiation, the transmit/receive times t1, t2, t3 are measured as described hereinbefore, and the thickness d of the calcaneus, ultrasonic wave propagation speed V in the calcaneus and assessment index E are computed based on this data as described in the foregoing embodiment to be displayed as point data 320. The health index 314 is displayed alongside.

According to this modification, there is no need to irradiate the whole bone with ultrasonic waves, and the time required for the measurement is thereby considerably reduced. The device may of course be provided with a switch enabling the operator to select either the foregoing embodiment or this modification as desired.

Figure 13:
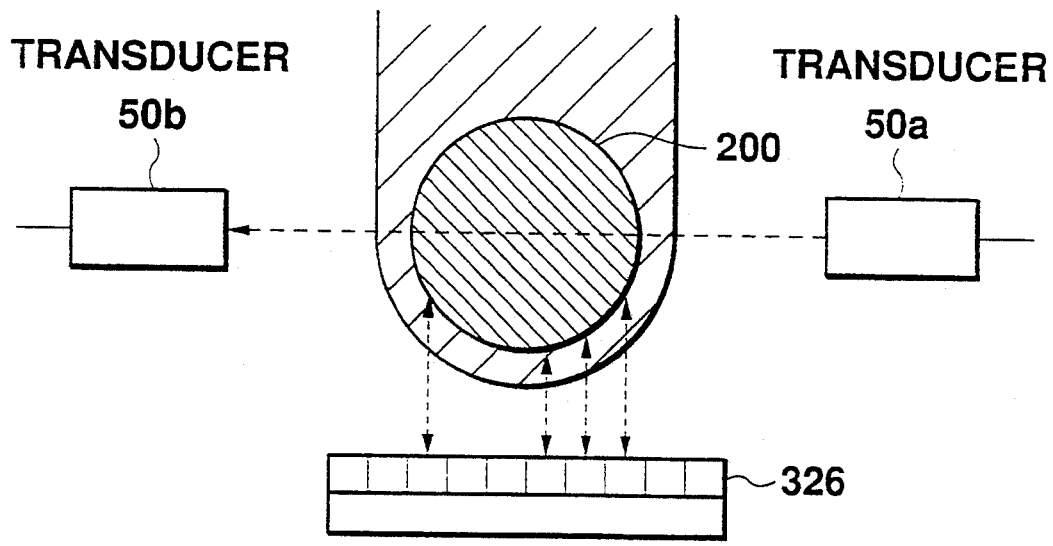
FIG. 13 is a drawing showing another method of measuring the bone thickness.

FIG. 13 shows a second embodiment for measuring thickness. According to this embodiment, an array transducer 326 is provided consisting of a plurality of ulrasonic transducers arranged in linear fashion. As shown in FIG. 13, a plurality of ultrasonic signals are transmitted in a direction perpendicular to the direction of the X-rays and ultrasonic beam. The thickness of the calcaneus 200 is then easily found from the signals received by the various transducers.

Figure 14:
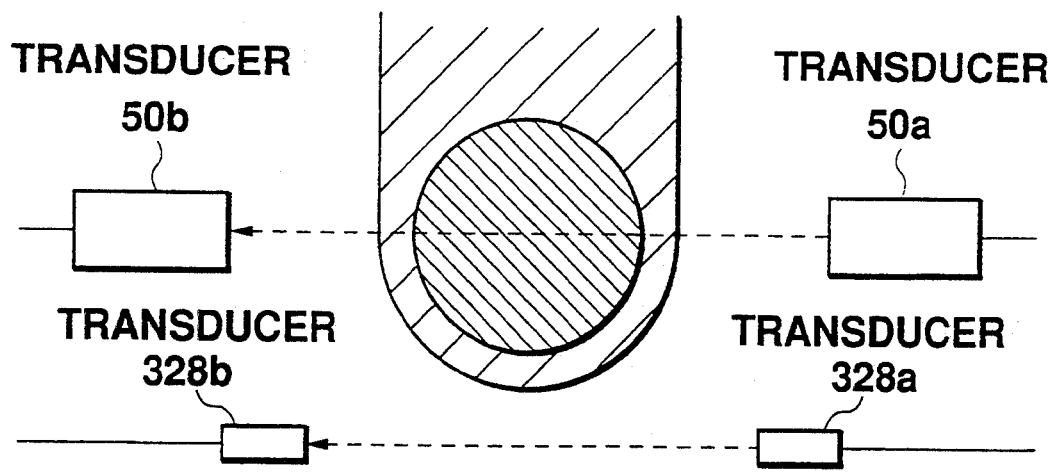
FIG. 14 is a drawing showing the measurement of the propagation speed of sound in water.

In the aforesaid embodiment, the calculation was performed assuming the value normally given for the speed of ultrasonic signals in water. In order to increase precision, however, it is desirable to provide a further pair of ultrasonic transducers 328a, 328b for making measurements in water as shown in FIG. 14.

(H) 2nd Embodiment of Measuring Unit

However, in the aforesaid apparatus, as shown in FIG. 3, some space in the water tank 46 must be reserved for the transducers 50a, 50b, consequently the size of the water tank 46 is increased. Further, as the X-rays travel a long distance in the water, there was a problem in that the X-rays became weaker (decrease of count rate).

In order to prevent decreased measurement precision, it is possible to increase the power of the X-rays. This is however undesirable in order to prevent increase in size of the X-ray generator 56, to lengthen its useful life and to avoid exposure of the operator to X-rays as far as possible.

It is also possible to install the X-ray generator 56 in the water tank, but it would then be necessary to make it watertight which requires a complex construction.

If widening of the X-ray beam generated by the X-ray generator is prevented, unnecessary exposure of other parts of the subject's body to X-rays can be reduced, and if interference by stray X-rays incident on the X-ray detector 58 can be prevented, the measurement precision can be increased. It is therefore desirable to collimate the X-rays sufficiently. Moreover, if the amount of water in the tank 46 can be reduced, it is less trouble to change the water in the tank and manage it, and the time required to change the water can be shortened.

In the embodiment described hereinafter, hollow immersible bodies (referred to hereafter as hollow bodies) are used.

Figure 15:
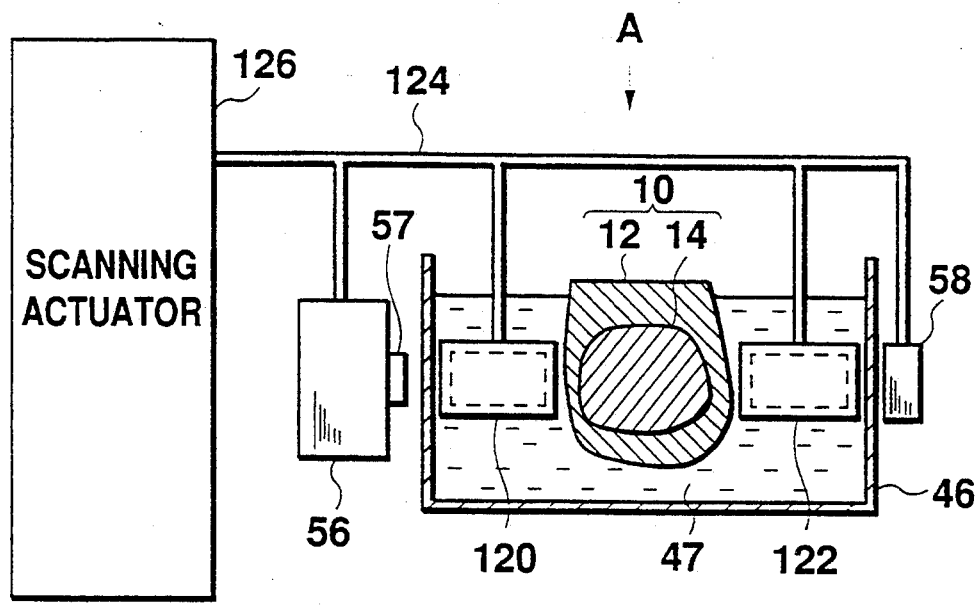
FIG. 15 is a drawing showing hollow bodies (i.e. immersible bodies) 120, 122 disposed in a water tank 46.
Figure 16:
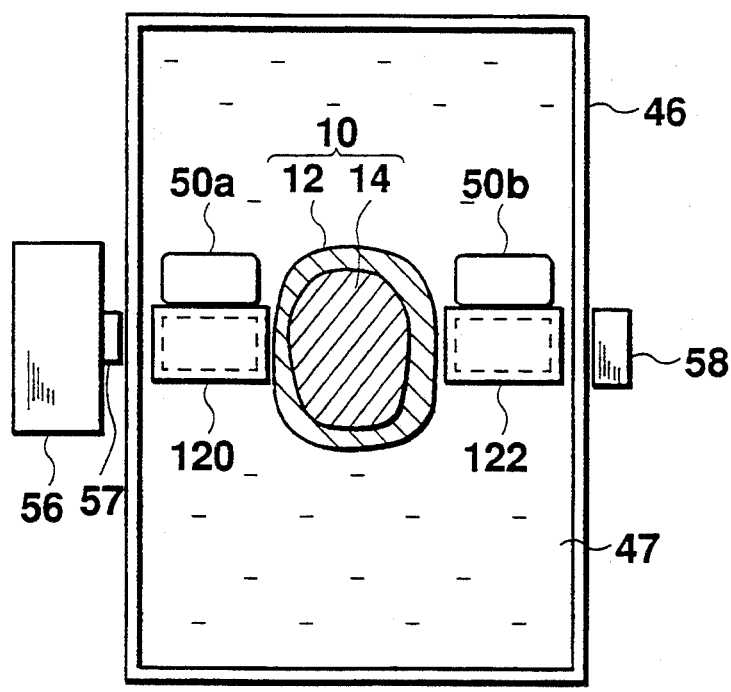
FIG. 16 is a drawing of the water tank 46 shown in FIG. 15 as seen from above.

FIG. 15 is a sectional view of the water tank 46 seen from the front, and FIG. 16 is a sectional view of the water tank 46 seen from the above.

As shown in FIG. 15, transducers 50a, 50b for transmitting and receiving ultrasonic waves are installed on either side of the subject's calcaneus (section) 10 in the water tank 46 containing water 47. These transducers are supported by arms 124 as shown in FIG. 15.

As shown in FIG. 15 and FIG. 16, the X-ray generator 56 and X-ray detector 58 are installed outside the water tank 46. A collimator 57 is installed at the X-ray radiation aperture of the X-ray generator 56. This X-ray generator 56 and X-ray detector 58 are supported by the arms 124.

The arms 124 are driven by a scanning actuator 126. According to this construction, the ultrasonic beam and X-ray beam can be moved to the part of the subject's body to be measured by ultrasonic waves and X-rays.

As shown in FIG. 15 and FIG. 16, the arms 124 support two cylindrical hollow bodies 120, 122 which sink in the water, and which more specifically are disposed in the path of the X-ray beam. The X-ray generator 56, the two hollow bodies 120, 122 and the X-ray detector 58 are arranged in a straight line.

FIG. 17 and FIG. 18 are enlarged views of the hollow bodies 120, 122. FIG. 17 is a lateral view, and FIG. 18 is a front view.

As shown in the figures, the bodies 120, 122 have hollow cavities and are sealed. The cavities are filled with air, but they may for example be under vacuum. By filling the cavities with a substance having a lower X-ray attenuation coefficient than the water 47, the X-ray attenuation coefficient can be reduced in comparison to the conventional apparatus.

It is preferable that the front plate F and rear plate R of the hollow bodies 120, 122 are made of a substance which has as low an X-ray attenuation coefficient as possible, for example acrylic material or the like. The side wall circumference S is made of a substance having an X-ray shielding effect and a high X-ray attenuation coefficient, for example metal.

The hollow body 120 can therefore be used instead of the collimator 57, and the hollow body 122 can be used to prevent stray X-rays from impinging on the X-ray detector 58. In such a case, the internal diameters of the hollow collimators 120, 122 are set to correspond to the width of the X-ray beam, for example 1 cm. The hollow bodies 120, 122 may however be chosen to have different internal diameters.

Measurements using the apparatus having the aforesaid construction are made as follows. As shown in FIG. 19, X-rays emitted by the X-ray generator 56 pass through the wall of the water tank 46, through the hollow body 120, through the subject 10, through the hollow body 122, and then again through the wall of the water tank 46 so as to reach the X-ray detector 58.

In the conventional case, the X-rays passed through water over the distances 130 shown in FIG. 19. According to this embodiment, however, the X-rays pass through air over the distances 130, so X-ray attenuation can be effectively prevented compared to the conventional case. Further, as each structural member is linked through the arms 124, the aforesaid situation can be maintained even if scanning is performed with the X-ray beam.

Further, the hollow bodies 120, 122 can be given collimating functions, widening of the X-ray beam can be effectively suppressed, and interference by stray X-rays can be prevented. External leakage of X-rays can therefore be prevented, and a precise measurement can be obtained. Moreover, as the amount of water in the water tank 46 can be reduced by the volume of the hollow bodies 120, 122, management of the water in the tank is rendered easier.

The hollow bodies 120, 122 may have various shapes, and rectangular parallelepiped bodies could for example be used.

What is claimed is:

1. A bone assessment apparatus comprising:
   means for measuring the propagation speed of sound in bone by passing ultrasonic waves through a test part of a subject's bone,
   means for measuring bone volume density by passing an X-ray beam of X-ray through said test part, and
   means for computing an assessment index for the bone based on said measured sound propagation speed and said measured bone volume density.

2. A bone assessment apparatus as defined in claim 1, wherein said propagation speed measuring means comprises:
   a pair of ultrasonic transducers for transmitting and receiving the ultrasonic waves through said test part,
   a thickness computer computing a thickness of the bone in a direction of the X-ray beam based on the waves received from said ultrasonic transducers, and
   a propagation speed computer computing the propagation speed of the ultrasonic waves by dividing an ultrasonic wave propagation time in the bone by said thickness; and wherein
   said bone volume density measuring means comprises:
   an X-ray generator for irradiating said test part with the X-rays,
   an X-ray detector for detecting the X-rays which have passed through said test part, and
   a density computer computing bone volume density based on an X-ray detection signal from said X-ray detector and said bone thickness.

3. A bone assessment apparatus as defined in claim 2, wherein said bone assessment index is the modulus of elasticity of the subject's bone.

4. A bone assessment apparatus as defined in claim 2, wherein said means for computing computes said bone assessment index based on a product of a square of said propagation speed of ultrasonic waves and said bone volume density.

5. A bone assessment apparatus as defined in claim 2 comprising a water tank for immersing said test part, and wherein said pair of ultrasonic transducers is disposed in said water tank.

6. A bone assessment apparatus as defined in claim 5, wherein said X-ray generator and said X-ray detector are outside said water tank.

7. A bone assessment apparatus as defined in claim 6 further comprising means for causing said pair of ultrasonic transducers, said X-ray generator and said X-ray detector to scan.

8. A bone assessment apparatus as defined in claim 7 further comprising a display connected to said assessment index computing means for displaying said bone assessment index.

9. A bone assessment apparatus as defined in claim 8 wherein said test part is the calcaneus.

10. A bone assessment apparatus as defined in claim 2 wherein said propagation speed measuring means measures the bone thickness by transmitting the ultrasonic waves through the subject's bone, and receiving the ultrasonic waves reflected from surfaces of the subject's bone.

11. A bone assessment apparatus as defined in claim 2 wherein said propagation speed measuring means measures the bone thickness by transmitting the ultrasonic waves from a direction perpendicular to the direction of the X-ray beam, and receiving the reflected ultrasonic waves.

12. A bone assessment apparatus for computing bone assessment indices using ultrasonic waves and X-rays, comprising:
    a water tank having a region for receiving a subject,
    a pair of ultrasonic transducers, one transducer being disposed on each side of said region inside said water tank,
    an X-ray generator and X-ray detector, one of these units being disposed on each side of said region outside said water tank, and
    a pair of immersible bodies, one immersible body being disposed on each side of said region in a path of X-rays inside said water tank, wherein said immersible bodies contain at least one of a substance having a lower X-ray attenuation coefficient than water and a vacuum within a sealed interior, and
    means for computing an assessment index based on signals produced by said ultrasonic transducers and said X-ray detector.

13. A bone assessment apparatus as defined in claim 12 further comprising side walls, wherein said side walls enclose the X-ray path and consist of a member which obstructs X-rays.

14. A bone assessment apparatus as defined in claim 13 wherein each of said immersible bodies is a hollow member having a cylindrical form.

15. A bone assessment apparatus as defined in claim 14 comprising a scanning mechanism displacing said two immersible bodies, and said scanning mechanism displaces said immersible bodies as an X-ray measurement point moves while maintaining said bodies in the path of the X-rays.

* * * * *